United States Patent
Zhang et al.

(10) Patent No.: US 11,555,811 B1
(45) Date of Patent: Jan. 17, 2023

(54) INTEGRATED RAPID NON-DESTRUCTIVE DETECTION SYSTEM FOR MULTI-INDEX OF MEAT QUALITY

(71) Applicant: INSTITUTE OF FOOD SCIENCE AND TECHNOLOGY, CHINESE ACADEMY OF AGRICULTURAL SCIENCE, Beijing (CN)

(72) Inventors: Dequan Zhang, Beijing (CN); Xiaochun Zheng, Beijing (CN); Li Chen, Beijing (CN); Shaobo Li, Beijing (CN); Xin Li, Beijing (CN); Chengli Hou, Beijing (CN)

(73) Assignee: INSTITUTE OF FOOD SCIENCE AND TECHNOLOGY, CHINESE ACADEMY OF AGRICULTURAL SCIENCES, Beijing (CN)

(*) Notice: Subject to any disclaimer, the term of this patent is extended or adjusted under 35 U.S.C. 154(b) by 0 days.

(21) Appl. No.: 17/661,557

(22) Filed: May 1, 2022

(51) Int. Cl.
*G01N 33/12* (2006.01)
*G01N 21/3563* (2014.01)
*G01N 21/359* (2014.01)

(52) U.S. Cl.
CPC ........... *G01N 33/12* (2013.01); *G01N 21/359* (2013.01); *G01N 21/3563* (2013.01)

(58) Field of Classification Search
CPC ... G01N 33/12; G01N 21/3563; G01N 21/359
(Continued)

(56) References Cited

U.S. PATENT DOCUMENTS

| 2014/0293277 A1* | 10/2014 | Subbiah | G01N 21/3563 356/300 |
| 2016/0169793 A1* | 6/2016 | Peng | G01N 21/474 250/214.1 |
| 2021/0311011 A1* | 10/2021 | Overcash | G06Q 30/0185 |

FOREIGN PATENT DOCUMENTS

| CN | 102507459 A | 6/2012 |
| CN | 104330382 A | 2/2015 |
(Continued)

OTHER PUBLICATIONS

Xiyu Wu et al, Study on the application of Near Infrared Spectroscopy in the meat quality evaluation. Science and Technology of Food Industry 11: 371-374, 380. Aug. 6, 2012.
(Continued)

*Primary Examiner* — Michael A Lyons
*Assistant Examiner* — Omar H Nixon
(74) *Attorney, Agent, or Firm* — CBM Patent Consulting, LLC

(57) ABSTRACT

An integrated rapid non-destructive detection system for multi-index of meat quality comprises a spectrometer for obtaining near-infrared spectra of a sample; an industrial tablet computer, comprising: a model embedding module for storing multiple prediction models; a model determining module connected with model embedding module and configured to call prediction model; an index prediction module connected with spectrometer and model determining module for receiving near-infrared spectra and predicting index data of the sample combining with called prediction model; wherein the number of detector elements of spectrometer is determined by an ultimate minimal resolution, and a resolution of the sample is controlled to the ultimate minimal resolution during an acquisition process; which realizes automatic black-white calibration, non-destructive detection
(Continued)

of multi-index, improves building efficiency of model, while maintaining building stability, and optimizes detection instrument volume.

9 Claims, 3 Drawing Sheets

(58) Field of Classification Search
USPC .......................................................... 702/19
See application file for complete search history.

(56) References Cited

FOREIGN PATENT DOCUMENTS

| CN | 105548062 A | 5/2016 |
|----|-------------|--------|
| WO | 2009005828 A1 | 1/2009 |

OTHER PUBLICATIONS

Wensong Wei et al, Rapid Determination of Content of Total Volatile Basic Nitrogen in Pork Based on Multispectral Detection System with Optimal Wavelength. Acta Optical Sinica vol. 37, No. 11:11300031-113000312. Nov. 30, 2017.

* cited by examiner

INTEGRATED RAPID NON-DESTRUCTIVE DETECTION SYSTEM FOR MULTI-INDEX OF MEAT QUALITY

TECHNICAL FIELD

The present disclosure relates to the technical field of rapid detection of meat quality. More specifically, the present disclosure relates to an integrated rapid non-destructive detection system for multi-index of meat quality.

BACKGROUND

Meat quality mainly includes edible quality, processing quality, nutritional quality and safety quality. Currently, evaluation methods for meat quality are mainly based on physical and chemical detection method and sensory evaluation method, wherein the results of the sensory evaluation method are not objective enough, and the physical and chemical detection method mainly adopts physical or chemical analysis methods to detect indexes of meat quality, these methods provide objective and credible detection results with high accuracy, but the pretreatment is cumbersome and the samples will be destructed, which is difficult to meet the requirement for short-term detection of large-scale samples in an actual production. Indexes used to evaluate the edible quality of meat mainly include color, tenderness, etc., the indexes used to evaluate the processing quality mainly include water holding capacity, pH, etc.; the indexes used to evaluate nutritional quality mainly include protein content, fat content, moisture content, UFA (unsaturated fatty acid), total contents of essential amino acid, etc.; and the indexes used to evaluate the safety quality mainly include total viable counts, total volatile basic nitrogen, biogenic amines, etc.

Near-infrared spectroscopy has been successfully used in the evaluation of meat quality in recent years, the patent application No. CN201510965311.6 discloses a rapid non-destructive detection method for multiple quality indexes of fresh beef, which achieves detecting six indexes simultaneously including cholesterol content, moisture content, fat content, protein content, shear force and water holding capacity of fresh beef by building a multi-prediction model. And there are still some problems to be solved. Firstly, multi-index detection would usually cause that a spectrometer needs more optical sensing components, resulting in large volume and high cost of the equipment. To reduce the volume and the cost of the equipment and meanwhile meets the need of multi-index detection is an urgent problem to be solved. Secondly, building a partial least squares regression prediction model of some index between the spectral data and the reference value of samples of calibration set usually faces the problems of large amount of spectral data and low modeling efficiency, which in particularly is more obvious for multi-index prediction.

SUMMARY

One object of the present disclosure is to solve the above problems and to provide advantages that will be described hereinafter at least.

Another object of the present disclosure is to provide an integrated rapid non-destructive detection system for multi-index of meat quality, which can detect the multi-index of meat quality non-destructively with advantageous effects of reducing the cost and the volume of the detection system.

In order to achieve these objects and other advantages according to the present disclosure, an integrated rapid non-destructive detection system for multi-index of meat quality is provided, comprising the following parts:

a spectrometer, which is configured to obtain near-infrared spectra of a meat sample;

an industrial tablet computer, which comprises:

a model embedding module, which is configured to store prediction models of multiple quality indexes;

a model determining module, which is connected to the model embedding module, and is configured to call at least one prediction model;

an index prediction module, which is connected with the spectrometer and the model determining module, and is configured to receive near-infrared spectra of the meat samples and then to predict the quality indexes of the meat samples by applying the prediction models;

wherein the number of detector elements of the spectrometer is determined according to an ultimate minimal resolution, which is settled and controlled when testing the quality indexes of the meat samples, and it is determined by the following steps:

S1, acquiring spectral data of each sample based on different resolution;

S2, predicting the number of the quality indexes of the system depend on the prediction models stored in the model embedding module, for any one of the quality indexes, using the spectral data with a series of resolution and the reference value of the quality index to build a series of prediction models based on chemometrics methods, and calculating a prediction correlation coefficient of corresponding model;

S3, determining an inflection point of the prediction correlation coefficient of any one of the quality indexes at different resolution, and a minimal resolution corresponding to this inflection point determined as the minimal resolution of the quality index;

S4, determining the maximum of the minimal resolution of all quality indexes as the ultimate minimal resolution.

Preferably, the multiple quality indexes determined include at least three indexes among following indexes such as meat color, tenderness, water holding capacity, pH, protein content, fat content, moisture content, total viable counts, total volatile basic nitrogen, UFA, total contents of essential amino acid, and biogenic amines;

wherein, a spectral range of 400-1100 nm is used to predict meat color, water holding capacity and the moisture content;

wherein, a spectral range of 900-1700 nm is used to predict tenderness, pH, the protein content and the fat content;

wherein, a spectral range of 400-1100 nm and 900-1700 nm are combined to predict total viable counts, the total volatile basic nitrogen, UFA, the total contents of essential amino acid, and the biogenic amines;

wherein, when acquiring spectral data includes 400-1100 nm and 900-1700 nm, the quality indexes are divided into group A (predicted by 400-1100 nm) and group B (predicted by 900-1700 nm), the ultimate minimal resolution are determined with above methods respectively.

dividing the multiple quality indexes into a group A with the acquisition range of 400-1100 nm and a group B with the acquisition range of 900-1700 nm, determining the ultimate minimal resolution corresponding to all quality indexes of the group A in the acquisition range of 400-1100 nm, and determining the ultimate minimal resolution corresponding to all quality indexes of the group B in the acquisition range of 900-1700 nm.

Preferably, the range of different resolution belong to the group A is 0.4-8 nm, and the range of different resolution belong to the group B is 15-45 nm.

Preferably, the prediction models of each quality index are built with following steps:

determining a sample set, and measuring the reference value of each quality index of each sample, wherein the genus of a sample in the sample set is the same as the genus of the meat samples;

determining the acquisition range according to the quality indexes of the meat samples, acquiring all near-infrared spectra of each sample, wherein the spectral data in the range of 400-1700 nm are obtained and merged by acquired near-infrared spectra of 400-1100 nm and 900-1700 nm to predict the total viable counts, the total volatile basic nitrogen, UFA, the total contents of essential amino acid, or biogenic amines;

calculating the differences of near-infrared spectra between adjacent peaks and troughs, sorting to be extracted characteristic spectra, and constructing the spectrogram with sort number as horizontal axis and the foresaid differences as vertical axis;

for any one of the quality indexes to be predicted, building the prediction model by using the characteristic spectra and the reference value of the quality index based on chemometric methods;

wherein the industrial tablet computer also comprises a spectral processing module, which is connected to the spectrometer and configured to extract the feature of spectra from acquired near-infrared spectra, and then the index prediction module receiving the extracted feature of spectra of the meat sample, and combining with the prediction model to predict quality index of the meat sample.

Preferably, the samples in a calibration set and a prediction set belong to the same genus, the samples in calibration set are collected from three breeds at least, samples of each breed include at least 5 kinds of month ages, samples of each month age include at least 5 parts, and samples of each part at least include time points of 45 min, 24 h, 72 h or 120 h after being slaughtered.

Preferably, the industrial tablet computer also comprises:

an adjusting module of reference, in which stored an average spectrum X and a spectral threshold have the same genus with the meat samples. the average spectral X, a local minimum reflectance spectrum (m) and a local maximum reflectance spectrum (M) are calculated based on at least 1000 pieces of near-infrared spectra of the samples belonging to the same genus with the meat samples to be predicted, and the spectral threshold is determined according to the average spectra X, the local minimum reflectance spectrum (m) and a local maximum reflectance spectrum (M);

a black-white adjusting module, which is connected with the adjusting module of reference and the spectrometer configured to obtain No. N+1 spectra of the meat samples after No. N spectra (N is set according to the characteristics of the meat sample), wherein the Mahalanobis distance is calculated between the average spectra X and the No. N+1 spectra, the No. N+1 spectra is determined whether it is normal or not by comparing the Mahalanobis distance and the spectral threshold, and on this account whether to carry out black-and-white adjust is controlled.

Preferably, the detection system also comprises:

a dark box, whose top is provided with a detection window, wherein the spectrometer is arranged in the dark box, a condensing lens and a light source are successively arranged below the detection window from top to bottom;

a black-white adjusting component, which comprises a disc rotationally arranged in the dark box and below the detection window, and a motor configured to drive the rotation of the disc; wherein the disc is provided with a white board, a black board and a through hole, and the motor is connected to the black-white adjusting module to control rotating the disc so that the white board, black board and the through hole are selectively coaxial with the detection window.

Preferably, the light source includes two halogen metal (aluminum or other) reflectors symmetrically arranged at 15-25 mm below the detection window, and the angle between the central axis of each reflector and the detection window is 55°-65°.

Preferably, the detection system also comprises: a result display module, which is connected to the index prediction module and configured to receive and display prediction results.

Preferably, the detection system also comprises: a data transmission module, which is connected to the index prediction module and configured to receive and transmit predicted index data to the user terminal.

The present disclosure at least includes the following advantageous effects:

1. The present disclosure realizes non-destructive detection of multiple quality indexes by embedding the multi-index prediction model. The detection system is provided with the black-white adjusting component and related black-white calibration module to realize the black-white adjust in initial or during the detection process. Wherein the black-white adjust during the detection process is implemented by the comparing result between average spectra X and spectral threshold, to make sure the necessary adjust requirements and to avoid the excessive time-consuming and laborious of over-adjusting.

2. The jump features of spectrum are extracted by the reflectivity intensity of wave peaks and troughs at certain regions of acquired near-infrared spectra, in order to improve the efficiency of building prediction models, stability of the model and efficiency in later detection of samples.

3. The local minimal resolution is determined based on one quality index, the ultimate local minimal resolution is determined based on multiple quality indexes, and then regard as an appropriate resolution of the system to achieve the objects of reducing cost and volume, while simplifying the control of detection operation conditions without reducing the detection accuracy, especially for multiple quality detection of large-scale samples.

Other advantages, objects and features of the present disclosure will be partially reflected by the following description, and will be partially understood by those skilled in this field through researching and practicing the present disclosure.

Reference signs: 1—detection window, 2—disc, 20—black board, 21—white board, 22—through hole, 3—condensing lens, 4—light source, 5—spectrometer, 6—industrial tablet computer, 7—dark box.

DETAILED DESCRIPTION

The present disclosure will be further described in detail hereinafter with reference to the accompanying drawings, so that those skilled in the art can implement the present disclosure with reference to the specification.

Figure 1:
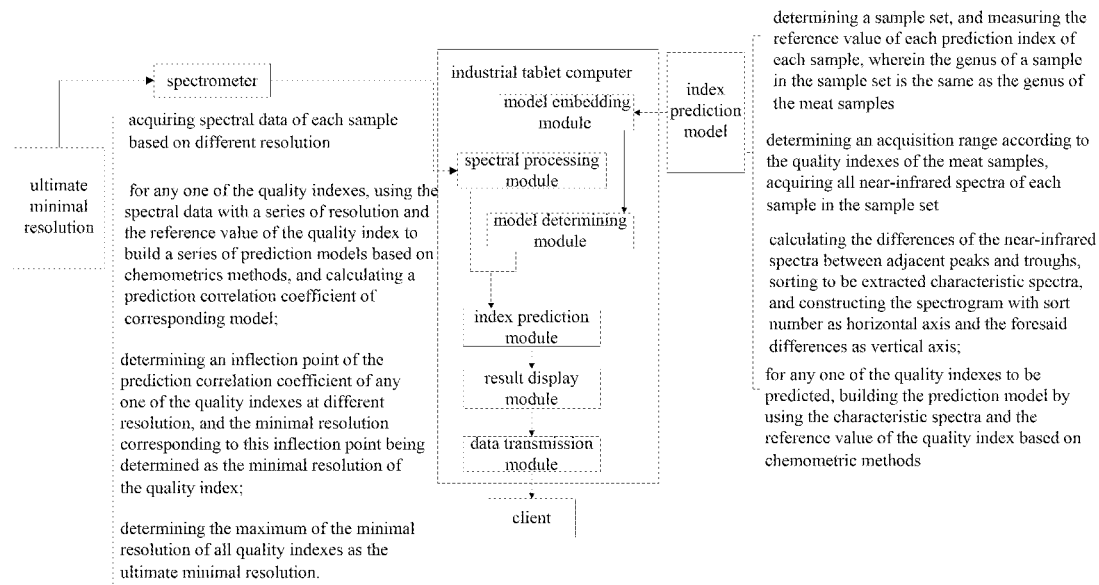
FIG. 1 is a flow chart of the integrated rapid non-destructive detection system for multi-index of meat quality according to one technical solution of the present disclosure.
Figure 3:
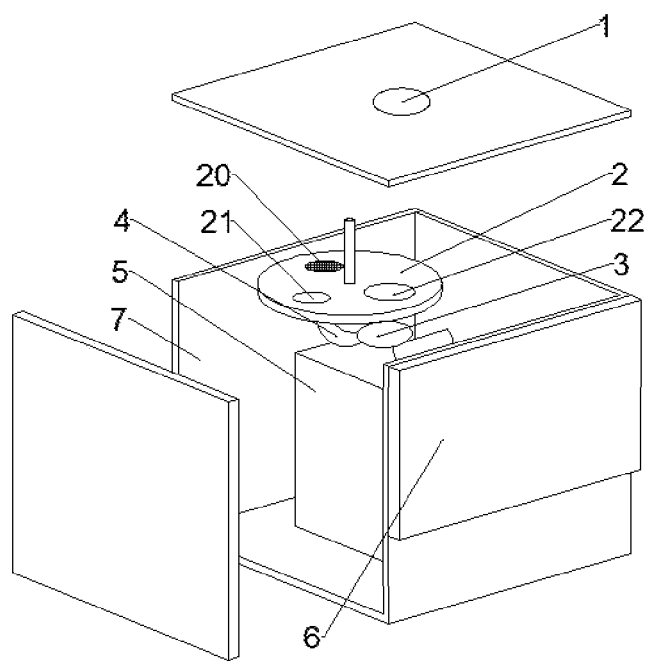
FIG. 3 is a structural diagram of the integrated rapid non-destructive detection system for multi-index of meat quality according to one technical solution of the present disclosure.

As shown in FIG. 1 and FIG. 3, the present disclosure provides an integrated rapid non-destructive detection system for multi-index of meat quality, comprising:

a spectrometer 5, which is configured to obtain near-infrared spectra (near-infrared spectrum) of a meat sample;

an industrial tablet computer 6, which comprises:

a model embedding module, which is configured to store multiple prediction models of multiple quality indexes;

a model determining module, which is connected with the model embedding module, and is configured to call at least one prediction model according to the detection requirements of the meat samples;

an index prediction module, which is connected with the spectrometer 5 and the model determining module, and is configured to receive near-infrared spectra of the meat samples from the spectrometer 5 and then to predict quality indexes of the meat samples combined with the called prediction model;

wherein, the number of detector elements of the spectrometer 5 is determined according to an ultimate minimal resolution, which is settled and controlled when testing the quality indexes of the meat sample, and it is determined by the following steps:

S1, acquiring spectral data of each sample based on different resolution;

S2, the number of quality indexes of the system can predict depend on the prediction models stored in the model embedding module. For any one of the quality indexes, the spectra with a series of resolutions and the reference value of the quality index can be used to build a series of prediction models based on chemometrics methods, and the prediction correlation coefficients of the corresponding prediction models can be calculated;

S3, determining an inflection point of the prediction correlation coefficient of any one of the quality indexes at different resolution, and the resolution corresponding to this inflection point being determined as the minimal resolution of the quality index;

S4, determining the maximum of the minimal resolution of all quality indexes as the ultimate minimal resolution.

In the above technical solution, the integrated rapid non-destructive detection system for multi-index of meat quality may be installed on cold chain trucks, in cold storage, or in supermarkets. The prediction models stored in the detection system may be set according to an actual application scene, simply that it fulfills the requirements of the actual application scene. After being installed, new prediction models may be embedded on the basis of meeting the ultimate minimal resolution according to the requirements of later detection. A response range of the spectrometer 5 is 400-1000 nm and/or 900-1700 nm, which is determined according to the quality indexes corresponding to the stored multiple prediction models. If the spectrometer 5 with the response range of 900-1700 nm is included, the detection system will be provided with a TEC for refrigeration and a fan for cooling. The number of detector elements of the spectrometer 5 is determined according to the ultimate minimal resolution. For example, if the ultimate minimal resolution of the range of 900-1700 nm is determined to be 32 nm, the number of the detector elements of the spectrometer 5 can be reduced to 25. That is, when the quality indexes are determined, the optimal number of the detector elements of the spectrometer 5 may be determined according to the ultimate minimal resolution. The chemometric method may be partial least squares regression or support vector machine regression algorithms. The non-destructive detection of the quality indexes is achieved by embedding the prediction models of the quality indexes in this technical solution. The minimal resolution is determined based on one quality index, and the ultimate minimal resolution of the spectrometer 5 is determined based on multiple quality indexes and is as an appropriate resolution to achieve the objects of reducing cost and volume of the detection instrument, meanwhile simplifying the control of detection operation conditions without reducing the detection accuracy, especially for multi-index detection of large scale of samples.

In another technical solution, wherein the quality indexes determined include at least three indexes among following indexes such as meat color, tenderness, water holding capacity, pH, protein content, fat content, moisture content, total viable counts, total volatile basic nitrogen, UFA, total contents of essential amino acid, and biogenic amines;

wherein a spectral range of 400-1100 nm is used to predict meat color, water holding capacity and the moisture content;

wherein a spectral range of 900-1700 nm is used to predict tenderness, pH, the protein content and the fat content;

wherein a spectral range of 400-1100 nm and 900-1700 nm are merged to predict the total viable counts, the total volatile basic nitrogen, UFA, the total contents of essential amino acid, and the biogenic amines;

wherein, when the acquisition range corresponding to the quality indexes simultaneously includes 400-1100 nm and 900-1700 nm, the quality indexes are divided into a group A with the acquisition range of 400-1100 nm, and a group B with the acquisition range of 900-1700 nm, the ultimate minimal resolution corresponding to all quality indexes of the group A in the acquisition range of 400-1100 nm is determined, and the ultimate minimal resolution corresponding to all quality indexes of the group B in the acquisition range of 900-1700 nm is determined. In the above technical solution, the spectrometer 5 is configured as:

(1) a single detector D1 with a response range (the acquisition range) of 400-1100 nm, which can be used for detecting the quality indexes including the meat color, the water holding capacity and the moisture content;

(2) a single detector D2 with a response range (the acquisition range) of 900-1700 nm, which can be used for detecting the quality indexes including the tenderness, pH, the protein content and the fat content;

(3) a dual detector, which is a collection of the single detector D1 and the single detector D2, which can be used for detecting the quality indexes including the meat color, the water holding capacity and the moisture content, the tenderness, pH, the protein content and the fat content, the total viable counts, the total volatile basic nitrogen, UFA, the total contents of essential amino acid, and the biogenic amines. The configuration of the spectrometer 5 is determined by adopting this technical solution.

In another technical solution, in a determination process of the ultimate minimal resolution corresponding to the quality indexes of the group A and group B, for group A:

A1, setting different resolution in a resolution range of 0.4-8 nm;

A2, determining whether the quality indexes of the group A include one of the total viable counts, the total volatile basic nitrogen, UFA, the total contents of essential amino acid, and the biogenic amines;

A3, if no, acquiring spectra of each sample based on different resolution (the acquisition range is 400-1100 nm), wherein, for any one of the quality indexes, the spectral data with a series of resolutions and the reference value of the quality index can be used to build series of prediction models based on chemometrics methods, and the prediction correlation coefficients of the corresponding prediction models can be calculated, determining an inflection point of the prediction correlation coefficients of any one of the quality indexes at different resolution, and the minimal resolution corresponding to this inflection point determined as the minimal resolution of the quality index;

A4, if yes, for the quality indexes (the acquisition range is 400-1100 nm), the same steps as mentioned above, determining the minimal resolution, for one of the total viable counts, the total volatile basic nitrogen, UFA, the total contents of essential amino acid, and the biogenic amines, a method for determining the minimal resolution includes:

A4a, acquiring spectra of each sample based on different resolution (the acquisition range is 400-1100 nm), and synchronously acquiring spectral data of the acquisition range of 900-1700 nm at a set resolution, wherein the set resolution is set according to the quality indexes and the experience of those skilled in this field, and may be determined by multiple detections;

A4b, performing spectral fusion of the near-infrared spectra of 400-1100 nm and 900-1700 nm to obtain near-infrared spectra covering wavelengths of 400-1700 nm, and determining the prediction correlation coefficient of the prediction model;

A4c, determining the inflection point of the prediction correlation coefficients of corresponding quality index at different resolution, and determining the resolution corresponding to the inflection point as an ultimate minimal resolution of the quality index;

For group B:

B1, setting different resolutions in a resolution range of 15-45 nm;

B2, determining whether the quality indexes of the group B include one of the total viable counts, the total volatile basic nitrogen, UFA, the total contents of essential amino acid, and the biogenic amines;

B3, if no, acquiring spectra of each sample based on different resolution (the acquisition range is 900-1700 nm), for any one of the quality indexes, the spectral data with a series of resolutions and the reference value of the quality indexes can be used to build series of prediction models based on chemometrics methods, and the prediction correlation coefficients of the corresponding models can be calculated, determining the inflection point of the prediction correlation coefficients of any one of the quality indexes at different resolution, and determining the resolution corresponding to this inflection point determined as the minimal resolution of the quality index;

B4, if yes, for the quality indexes (the acquisition range is 900-1700 nm), the same steps as mentioned above, determining the minimal resolution, for one of the total viable counts, the total volatile basic nitrogen, UFA, the total contents of essential amino acid, and the biogenic amines, a method for determining the minimal resolution includes:

B4a, acquiring spectral data of each sample based on different resolution (the acquisition range is 900-1700 nm), and synchronously acquiring spectral data of the acquisition range of 400-1100 nm at a set resolution, wherein the set resolution is set according to the quality indexes and the experience of those skilled in the field, and may be determined by multiple detections;

B4b, performing spectral fusion of near-infrared spectra of 400-1100 nm and 900-1700 nm to obtain near-infrared spectra covering wavelengths of 400-1700 nm, and determining the prediction correlation coefficient of the prediction model;

B4c, determining the inflection point of the prediction correlation coefficients of corresponding quality index at different resolution, and the resolution corresponding to this inflection point determined as the minimal resolution of the quality index. By adopting this technical solution, different resolution ranges are determined for different acquisition ranges, and the minimal resolution of the quality index corresponding to the acquisition range in the resolution range is determined. The minimal resolution for the acquisition range covering wavelengths of 400-1700 nm is determined by dividing the acquisition range, which improves the detection accuracy of the whole device and avoid the influence of irrelevant acquisition ranges on the accuracy of detection results.

In another technical solution, a building method of each prediction model includes the following steps:

determining a sample set, and measuring the reference value of each quality index of each sample, wherein the genus of the samples in a calibration set is the same as the genus of the meat samples in a prediction set. Specifically, the genus of beef samples is Bos genus, the genus of pork samples is pig genus, the genus of mutton samples is *Ovis*, etc. That is, the meat sample is can be divided into pork, beef, mutton, chicken, duck and goose according to their genera. A determination method of the reference value of each quality index is detailed in Table 1:

TABLE 1

Summary of determination method of the reference value of indexes of meat

| Meat quality | Indexes | National/industrial determination standards and references |
|---|---|---|
| Edible quality | Meat color | Zając M, Zając K, Dybáś J. The effect of nitric oxide synthase and arginine on the color of cooked meat[J]. Food Chemistry, 2022, 373 |
| | Tenderness | NY/T 1180-2006, "measurement method of tenderness, shear force measurement method" |
| Proc-essing quality | Water holding capacity | Xiao X, Hou C, Zhang D, et al. Effect of pre- and post-rigor on texture, flavor, heterocyclic aromatic amines and sensory evaluation of roasted lamb[J]. Meat Science, 2020, 169(3): 108-220 |
| | pH | Szerman N, Rao W L, Li X, et al. Effects of the Application of Dense Phase Carbon Dioxide Treatments on Technological Parameters, Physicochemical and Textural Properties and Microbiological Quality of Lamb Sausages[J]. Food Engineering Reviews, 2015, 7(2). |

TABLE 1-continued

Summary of determination method of the reference value of indexes of meat

| Meat quality | Indexes | National/industrial determination standards and references |
|---|---|---|
| Nutritional quality | Protein content | GB/T 5009.5-2010, "National food safety standard, determination of protein in foods" |
| | Fat content | GB/T 9695.7-2008, "Determination of total fat content in meat or meat products" |
| | Moisture content | GB/T 9695.15-2008, "Determination of moisture content in meat or meat products" |
| | UFA (unsaturated fatty acids) | GB 5009.168-2016, National food safety standard, determination of fatty acids in foods |
| | Total contents of essential amino acid | GB 5009.124-2016, National food safety standard, determination of amino acids in foods |
| Safety quality | Total viable counts | GB 4789.2-2016, National food safety standard, food biological examination, determination of total viable counts |
| | Total volatile basic nitrogen | GB 5009.228-2016, National food safety standard, determination of total volatile basic nitrogen in foods |
| | Biogenic amines | GB 5009.208-2016, National food safety standard, determination of biogenic amines in foods | determining the acquisition range according to the quality indexes, acquiring all near-infrared spectra of each sample in the sample set in the acquisition range, and when the quality indexes are at least one of the total viable count, the total volatile basic nitrogen, UFA, the total contents of essential amino acid and the biogenic amines, for corresponding quality indexes, performing spectral fusion of the near-infrared spectra of 400-1100 nm and 900-1700 nm to obtain the near-infrared spectra covering wavelengths of 400-1700 nm;

calculating the differences of each near-infrared spectra between adjacent peaks and troughs according to the reflection value of wavelength as extracted characteristic spectra, sorting from small to large, and constructing the spectrogram with sort number as horizontal axis and the foresaid differences as vertical axis;

for any one of the quality indexes to be predicted, building the prediction model by using the characteristic spectra and the reference value of the quality index based on chemometric methods;

wherein the industrial tablet computer 6 also comprises a spectral processing module, which is connected to the spectrometer 5, and is configured to extract the characteristic spectra from acquired near-infrared spectra;

an index prediction module, which is connected with the spectral processing module and the model determining module, and is configured to receive the characteristic spectra of the samples, and then to predict the quality indexes of the meat samples by applying the prediction models. In the above technical solution, take the called prediction models, including a prediction model corresponding to the protein content, a prediction model corresponding to the fat content, a prediction model corresponding to the total viable counts, as an example, there are two prediction methods for the quality indexes, as follows:

the first prediction method, when the near-infrared spectra is used in the building process of the called prediction model;

when the quality index is the protein content, the protein content of the samples being predicted by using the near-infrared spectra in the range of 900-1700 nm combining with the called prediction model corresponding to the protein content;

when the quality index is the fat content, the fat content of the samples being predicted by using the near-infrared spectra in the range of 900-1700 nm combining with the called prediction model corresponding to the fat content;

when the quality index is the total viable counts, the total viable counts of the samples being predicted by using the near-infrared spectra covering wavelengths of 400-1700 nm obtained by performing spectral fusion of near-infrared spectra of 400-1100 nm and 900-1700 nm, combining with the called prediction model corresponding to the total viable counts;

the second prediction method, when the characteristic spectra is used in the building process of the called prediction model;

when the quality index is the protein content, the protein content of the samples being predicted by using the characteristic spectra in the range of 900-1700 nm combining with the called prediction model corresponding to the protein content;

when the quality index is the fat content, the fat content of the samples being predicted by using the characteristic spectra in the range of 900-1700 nm combining with the called prediction model corresponding to the fat content;

when the quality index is the total viable counts, performing spectral fusion of the near-infrared spectra of 400-1100 nm and 900-1700 nm to obtain the near-infrared spectra covering wavelengths of 400-1700 nm, obtaining a characteristic spectra according to the near-infrared spectra covering wavelengths of 400-1700 nm, predicting the total viable counts of the samples by the characteristic spectra combining with the called prediction model corresponding to the total viable counts. The second prediction method is adopted relative to the first prediction method, for the acquired near-infrared spectra, and the reflectivity intensity differences of wave peaks and troughs of near-infrared spectral wave at certain region are used to extract spectrum jump features, improve the efficiency of building prediction models, stability of the prediction model and efficiency in later detection of the meat samples.

In another technical solution, the samples in a calibration set and a prediction set belong to the same genus, the samples in the calibration set are collected from three breeds at least, samples of each breed include at least 5 kinds of month ages, samples of each month age include at least 5 parts, and samples of each part at least include time points of 45 min, 24 h, 72 h or 120 h after being slaughtered. In the above technical solution, the breeds of the samples in the sample set are at least three, samples of each breed include at least 5 kinds of month ages, samples of each month age include at least 5 parts, and samples of each part at least include time points of 45 min, 24 h, 72 h or 120 h after being slaughtered. The technical solution solves the problems that most traditional prediction models of meat are built only based on a sample set with high degree of homogeneity, that is, the sample set is constructed based on single breed, single month age, single part, or samples obtained at single time point, so that the built prediction model has restrictive applicability and robustness, which limits the application of near-infrared spectroscopy in the field of the quality prediction of meat, also limits the online and practicality of non-destructive quality prediction system of meat. Conversely, the sample set is comprehensively determined in a determination process of the sample, which can improve the practicality of non-destructive quality prediction system of meat.

In another technical solution, the industrial tablet computer 6 also comprises:

an adjusting module of reference, in which an average spectrum X and a spectral threshold having the same genus with the samples, wherein, the average spectral X, a local minimum reflectance spectrum (m) and a local maximum reflectance spectrum (M) are calculated based on at least 1000 near-infrared spectra of the samples belonging to the same genus with the samples, and the spectral threshold is determined according to the average spectral X, the local minimum reflectance spectrum (m) and the local maximum reflectance spectrum (M);

a black-white adjusting module, which is connected with the adjusting module of reference and the spectrometer 5, is configured to obtain No. N+1 spectra of the meat samples after the spectrometer 5 obtains No. N spectra (N is set according to the characteristics of the sample), wherein the Mahalanobis distance is calculated between the average spectra X and the No. N+1 spectra, the No. N+1 spectra is determined whether it is normal or not by comparing the Mahalanobis distance and the spectral threshold. if yes, determining the No. N+1 spectra being normal, taking the No. N+1 as No. 1, the spectrometer 5 continuously obtaining the near-infrared spectra of the samples to set times N, continuously determining; if no, re-determining the No. N+1 spectra after calibration. In the above technical solution, the black-white adjusting module is also used for initial calibration, and N is preferably 45-55, further preferably 50. In this technical solution, the detection system is provided with an auto black-white adjusting component and related black-white adjusting module to realize the black-white calibration in the initial or during the detection process; wherein the black-white calibration during the detection process is determined according to the average spectral X and the spectral threshold, which avoid excessive time-consuming and laborious calibration, while meeting the calibration requirements.

Figure 2:
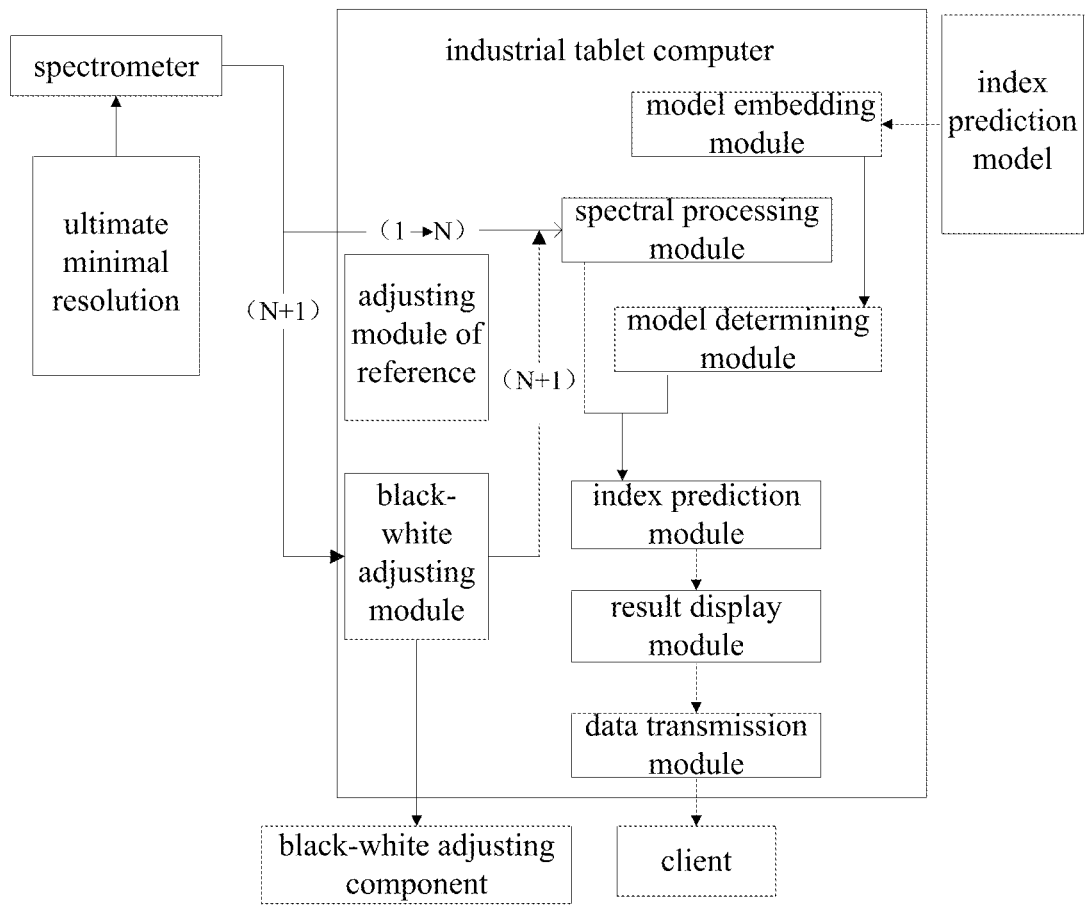
FIG. 2 is a flow chart of the integrated rapid non-destructive detection system for multi-index of meat quality according to another technical solution of the present disclosure.

In another technical solution, as shown in FIGS. 2 and 3, the integrated rapid non-destructive detection system for multi-index of meat quality also comprises:

a dark box 7, wherein the spectrometer 5 is arranged in the dark box 7, a detection window 1, which is arranged on the top of the dark box 7;

a light source 4, which is symmetrically placed under the detection window 1 at a certain angle;

a condensing lens 3, which is arranged between the light source 4 and the detection window 1;

a black-white adjusting component, which comprises a disc 2 that is rotationally arranged in the dark box 7 and below the detection window 1, and a motor configured to drive the rotation of the disc 2; wherein the disc 2 is provided with a white board 21, a black board 20 and a through hole 22;

wherein the motor is connected to the black-white adjusting module for controlling the motor to rotate the disc 2 so that the white board 21, the black board 20 and the through hole 22 are selectively coaxial with the detection window 1. In the above technical solution, the dark box 7 is preferably cubic, the detection window 1 is a circle with a diameter of about 40 mm, and the detection window 1 is made of quartz glass sheet and is flush with the equipment shell. The detection window 1 not only can be a platform for placing the samples, but also a window for acquiring spectral information of the samples. The light from the light source 4 irradiates the sample at a certain angle, is gathered through the condensing lens 3, and is transmitted to the spectrometer 5. The black-white adjusting component is used to cooperate with the black-white adjusting module to realize the initial black-white calibration and the intermediate black-white calibration of the system. The radius of the through hole 22 is greater than the radius of the detection window 1. In an acquisition process of near-infrared spectra of the samples, the motor drives the disc 2 to rotate so that the through hole 22 is arranged coaxially with the detection window 1. In a calibration process with the white board 21, the motor drives the disc 2 to rotate so that the white board 21 is arranged coaxially with the detection window 1. In a calibration process with the black board 20, the motor drives the disc 2 to rotate so that the black board 20 is arranged coaxially with the detection window 1. The condensing lens 3 is arranged between the light source 4 and the detection window 1, and is used to gather and collimate the spectrum reflected by the samples, so that the spectral information reflected by the samples is radiated into a slit of the spectrometer 5 as much as possible, which can improve the signal-to-noise ratio and reduce the exposure time of the spectrometer 5. A specific operation process includes:

(1) switching on the power of the detection system;
(2) placing the samples on the detection window 1;
(3) operating the industrial tablet computer 6 to start detection, including the following steps:

opening the detection software on the industrial tablet computer 6 to automatically detect the connection of each hardware and each module, after it is normal, selecting the genus of the samples and the quality indexes;

the system determining the selection of the single detector D1, the single detector D2 or the dual detector (the single detector D1 and the single detector D2) according to set genus of the samples, the quality index number and range of the quality indexes; if the quality indexes include one of the meat color, the water holding capacity and the moisture content, selecting the single detector D1, if the quality indexes include one of the tenderness, pH, the protein content and the fat content, selecting the single detector D2, if the quality indexes include one of the total viable counts, the total volatile basic nitrogen, UFA, the total contents of essential amino acid, or the biogenic amines, selecting the dual detector, wherein for this type of quality indexes, the determination of this type of the quality indexes needs to call the spectral fusion algorithm for spectral fusion;

taking the quality indexes including the protein content, the fat content and the total viable counts as an example as follows, selecting the dual detector;

determining the prediction models to be called (a prediction model corresponding to the protein content, a prediction model corresponding to the fat content, and a prediction model corresponding to the total viable counts) according to a meat sample and the quality indexes, starting the model embedding module to transfer the data of relevant prediction models into a cache;

when starting for the first time, clicking a "start detection" button to carry out the initial black-white calibration, and calling the black-white adjusting module to perform the initial black-white reference calibration;

acquiring the near-infrared spectra of the samples in the acquisition range of 400-1100 nm by a spectrometer 5D1, wherein the resolution of the spectrometer 5D1 is the ultimate minimal resolution of the acquisition range of 400-1100 nm during the acquiring process;

acquiring the near-infrared spectra of the samples in the acquisition range of 900-1700 nm by a spectrometer 5D2, wherein the resolution of the spectrometer 5D2 is the ultimate minimal resolution of the acquisition range of 900-1700 nm during the acquiring process;

predicting the index data of the samples according to the near-infrared spectra of the samples, combining with at least one called prediction model;

wherein the black-white adjusting component comprises the disc 2 that is rotationally arranged in the dark box 7 and located below the detection window 1, and a motor disposed to drive the rotation of the disc 2; wherein the disc 2 is provided with a white board 21, a black board 20 and a through hole 22. In an acquisition process of near-infrared spectra of the samples, the motor drives the disc 2 to rotate so that the through hole 22 is arranged coaxially with the detection window 1. In a calibration process with the white board 21, the motor drives the disc 2 to rotate so that the white board 21 is arranged coaxially with the detection window 1. In a calibration process with the black board 20, the motor drives the disc 2 to rotate so that the black board 20 is arranged coaxially with the detection window 1. In this technical solution, the cooperation of the motor and the disc 2 is convenient for the black-white calibration.

In another technical solution, the light source 4 includes halogen metal (aluminum or other) reflectors symmetrically arranged at 15-25 mm below the detection window 1, and the central axis of each reflector lamp cup is 55°-65° to the central axis of the detection window 1. The power of the reflector is 5 W to provide near-infrared light in a range of 300-2500 nm, and it is preferred that the light source 4 is arranged 20 mm below the detection window 1. In this technical solution, the two reflectors are arranged in distribution status. On the one hand, a sufficient space is provided for the condensing lens 3, and on the other hand, the light source 4 of the two reflectors are focused on the detection window 1 to form a light spot with a certain size (specifically within a range of 10-20 mm).

In another technical solution, the integrated rapid non-destructive detection system for multi-index of meat quality also comprises: a result display module, which is connected with the index prediction module, and is configured to receive and display prediction results. In the technical solution, the industrial tablet computer 6 is provided with an operation screen that can realize an input function of relevant signals in the whole detection process, and synchronously realizes the function of receiving and displaying the prediction results.

In another technical solution, the integrated rapid non-destructive detection system for multi-index of meat quality also comprises: a data transmission module, which is connected with the index prediction module, and is configured to receive and transmit predicted index data to the user terminal. The data transmission module receives the index data predicted by the index prediction module, and transmit received index data to the user terminal (a mobile phone, a computer, etc.) based on WIFI or Bluetooth. The index data can be displayed on an APP program interface of the user terminal, and the industrial tablet computer 6 can be remotely controlled by the user terminal to realize the detection function using the detection system. By adopting this technical solution, a communication connection with the user terminal is established to facilitate remote reception and control.

Embodiment 1

A rapid non-destructive detection method of multi-index of meat quality, includes the following steps:

step one, determination of the minimal resolution:

determining multiple quality indexes to be predicted, including meat color, the water holding capacity, the protein content, the fat content, the moisture content, the total viable counts, the total volatile basic nitrogen, and the biogenic amines;

determining the ultimate minimal resolution of the acquisition range of 400-1100 nm being 2.8 nm according to the above multiple quality indexes; wherein the inflection point corresponding to the multiple quality indexes in the corresponding acquisition range is as Table 2 below;

TABLE 2

The minimal resolution of the acquisition range of 400-1100 nm

| Quality indexes | Meat color | Water holding capacity | Moisture content |
| --- | --- | --- | --- |
| Inflection point | 3.8 nm | 4.1 nm | 4.6 nm |
| Quality indexes | Total viable counts | Total volatile basic nitrogen | Biogenic amines |
| Inflection point | 3.5 nm | 2.8 nm | 4.6 nm | determining the ultimate minimal resolution of the acquisition range of 900-1700 nm being 26 nm according to the above multiple quality indexes; wherein the inflection point corresponding to the multiple quality indexes in the corresponding acquisition range is as Table 3 below;

TABLE 3

The minimal resolution of the acquisition range of 900-1700 nm

Figure 4:
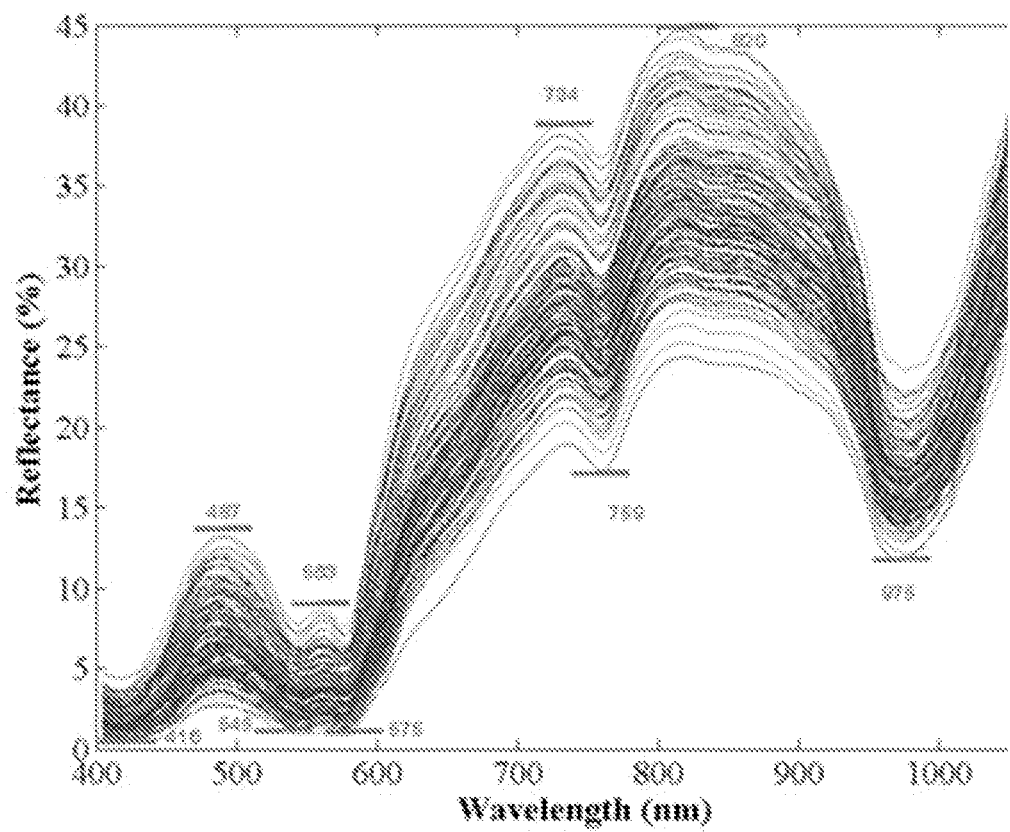
FIG. 4 is a near-infrared spectrum according to one technical solution of the present disclosure.
Figure 5:
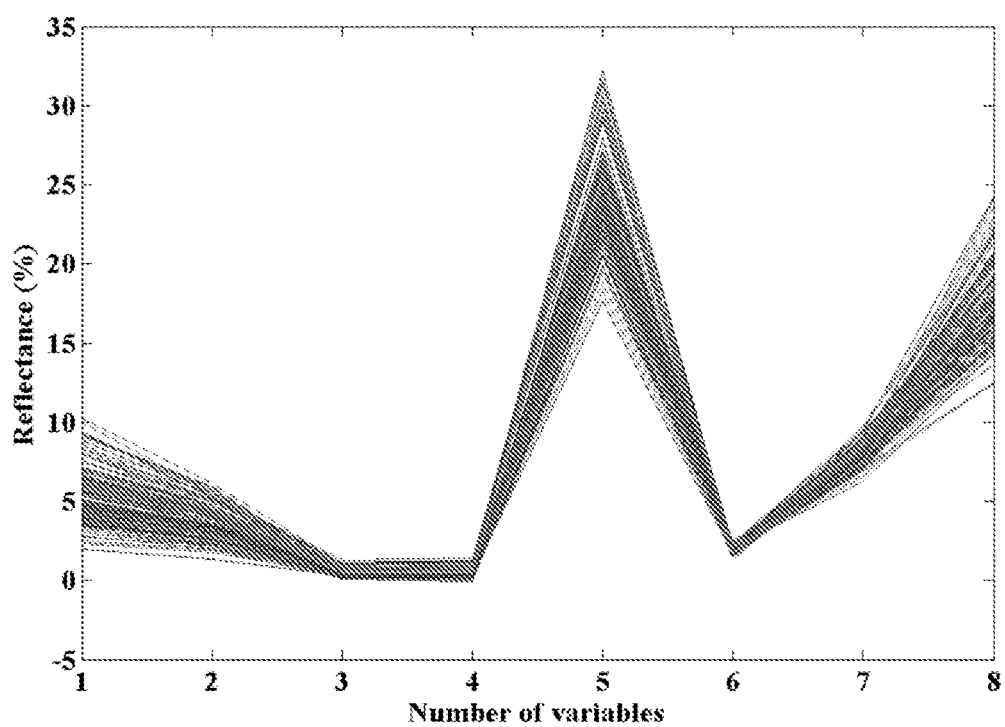
FIG. 5 is characteristic spectra according to one technical solution of the present disclosure.

| Quality indexes | Protein content | Fat content | |
| --- | --- | --- | --- |
| Inflection point | 32 nm | 32 nm | |
| Quality indexes | Total viable counts | Total volatile basic nitrogen | Biogenic amines |
| Inflection point | 26 nm | 32 nm | 40 nm | step two, determining the number of detector elements of the spectrometer based on the minimal resolution, and building an integrated rapid non-destructive detection system for multi-index of meat quality, wherein the model embedding module of the industrial tablet computer of the detection system is stored with the prediction models that is in one-to-one correspondence with meat color, the water holding capacity, the protein content, the fat content, the moisture content, the total viable counts, the total volatile basic nitrogen, and the biogenic amines; wherein, for any one of the quality indexes, a building method of the prediction model includes:

2.1, selection of samples selecting three breeds of sheep, randomly selecting five sheep of different ages, and selecting meat samples of shoulder, outside, knuckle, backstrap, flap from slaughtered sheep carcass at time points of 45 min, 24 h, 72 h or 120 h after being slaughtered as a sample set;

2.2 obtaining the near-infrared spectra of each sample in the acquisition ranges of 400-1100 nm and 900-1700 nm with corresponding ultimate minimal resolution as an acquisition resolution, and performing spectral fusion of the near-infrared spectra of 400-1100 nm and 900-1700 nm to obtain the merged near-infrared spectra within a wavelength range of 400-1700 nm;

2.3, determining the reference value of each sample corresponding to the multiple quality indexes, wherein the obtained reference values of each sample include: meat color, the water holding capacity (boiling loss), the protein content, the fat content, the moisture content, the total viable counts, the total volatile basic nitrogen, and the biogenic amines;

2.4, for the near-infrared spectra corresponding to each sample, calculating the differences of each near-infrared spectra between adjacent peaks and troughs according to the reflection value of wavelength as extracted characteristic spectra, sorting from small to large, and constructing the spectrogram with sort number as horizontal axis and the foresaid differences as vertical axis; as shown in FIG. 4-5, taking the near-infrared spectra in the acquisition ranges of 400-1100 nm as an example, the adjacent peaks and troughs forming a peak-trough pair, as shown in Table 4 below:

TABLE 4

Related data of the characteristic spectra

| Peak-trough pairs | Difference (%) range | Sorting number |
|---|---|---|
| (Trough 416 nm, peak 487 nm) | 4-11 | 1 |
| (Peak 487 nm, trough 545 nm) | 3-10 | 2 |
| (Trough 545 nm, peak 563 nm) | 3-4 | 3 |
| (Peak 563 nm, trough 575nm) | 3-5 | 4 |
| (Trough 575 nm, peak 734 nm) | 20-35 | 5 |
| (Peak 734 nm, trough 759 nm) | 4-5 | 6 |
| (Trough 759 nm, peak 820 nm) | 9-12 | 7 |
| (Peak 820 nm, trough 975 nm) | 15-25 | 8 | in the above Table 4, a range of the difference being the given range of difference corresponding to all near-infrared spectra under the condition of corresponding peak-trough pair;

2.5, for any one of the quality indexes to be predicted, building the prediction model by using the characteristic spectra and the reference value of the quality index based on chemometric methods;

2.6, embedding the built prediction model into the model embedding module of the integrated rapid non-destructive detection system for multi-index of meat quality;

2.7, for the samples to be detected, wherein the samples to be detected has two, including sample 1 (backstrap meat from 8-month-old Ningxia Tan-sheep at time point of 45 after being slaughtered), and sample 2 (outside meat from 8-month-old Ningxia Tan-sheep at time point of 45 after being slaughtered);

when the quality indexes are meat color, the water holding capacity, and the moisture content, predicting meat color, the water holding capacity, and the moisture content of the samples by the characteristic spectra in the range of 400-1100 nm and called prediction models corresponding to meat color, the water holding capacity, and the moisture content;

when the quality indexes are the protein content and the fat content, predicting the protein content and the fat content of the samples by the characteristic spectra in the range of 900-1700 nm and called prediction models corresponding to the protein content and the fat content;

when the quality index are the total viable counts, the total volatile basic nitrogen, and the biogenic amines, predicting the total viable counts, the total volatile basic nitrogen, and the biogenic amines of the samples by the characteristic spectra in the range of 400-1700 nm and called prediction models corresponding to the total viable counts, the total volatile basic nitrogen, and the biogenic amines; shown as Table 5 below:

TABLE 5

Comparison of prediction value of the quality indexes and reference value of sample 1 and sample 2 by the method of Embodiment 1

| Quality indexes | Sample 1 | | | Sample 2 | | |
|---|---|---|---|---|---|---|
| | Reference value | Prediction value | Absolute deviation | Reference value | Prediction value | Absolute deviation |
| Meat color (L*, dimensionless) | 46.37 | 45.65 | 0.72 | 44.27 | 42.71 | 1.56 |
| Water holding capacity | 16.60 | 17.28 | 0.68 | 17.33 | 18.07 | 0.74 |
| Moisture content (%) | 76.18 | 76.84 | 0.66 | 76.12 | 76.53 | 0.41 |
| Protein content (%) | 28.45 | 29.74 | 1.29 | 17.31 | 18.03 | 0.72 |
| Fat content (%) | 3.26 | 3.15 | 0.11 | 1.20 | 1.16 | 0.04 |
| Total viable counts (logcfu/g) | 3.95 | 3.75 | 0.20 | 3.68 | 3.55 | 0.13 |
| Total volatile basic nitrogen (mg/100 g) | 9.57 | 9.23 | 0.34 | 12.34 | 11.96 | 0.38 |
| Biogenic amines (cadaverine, mg/100 g) | 28.63 | 27.63 | 1.00 | 31.33 | 32.32 | 0.99 |

Comparative Example 1

A rapid non-destructive detection method of multi-index of meat, includes the following steps:

step one, determining the minimal resolution, same step as the step one of Embodiment 1;

step two, determining the number of detector elements of the spectrometer based on the minimal resolution, and building an integrated rapid non-destructive detection system for multi-index of meat quality, wherein a model embedding module of an industrial tablet computer of the detection system is stored with the prediction models that is in one-to-one correspondence with meat color, the water holding capacity, the protein content, the fat content, the moisture content, the total viable counts, the total volatile basic nitrogen, and the biogenic amines; wherein, for any one of the quality indexes, a building method of the prediction model includes:

2.1, selection of samples, same step as the step 2.1 of Embodiment 1;

2.2, same step as the step 2.2 of Embodiment 1;

2.3, same step as the step 2.3 of Embodiment 1;

no including step 2.4 of Embodiment 1;

2.5, for any one of the quality indexes, building the prediction model corresponding to the quality index according to the near-infrared spectra and the reference value corresponding to the quality index by a chemometric method;

2.6, embedding the built prediction model into the model embedding module of the integrated rapid non-destructive detection system for multi-index of meat quality;

2.7, for the samples to be detected when the quality indexes are meat color, the water holding capacity, and the moisture content, predicting meat color, the water holding capacity, and the moisture content of the samples by the near-infrared spectra in the range of 400-1100 nm and called prediction models corresponding to meat color, the water holding capacity, and the moisture content;

when the quality indexes are the protein content and the fat content, predicting the protein content and the fat content of the samples by the near-infrared spectra in the range of 900-1700 nm and called prediction models corresponding to the protein content and the fat content;

when the quality index are the total viable counts, the total volatile basic nitrogen, and the biogenic amines, predicting the total viable counts, the total volatile basic nitrogen, and the biogenic amines of the samples by the near-infrared spectra in the range of 400-1700 nm and called prediction models corresponding to the total viable counts, the total volatile basic nitrogen, and the biogenic amines; shown as Table 6 below:

TABLE 6

Comparison of prediction value of the indexes and reference value of sample 1 and sample 2 by the method of Comparative example 1

| Quality indexes | Sample 1 | | | Sample 2 | | |
|---|---|---|---|---|---|---|
| | Reference value | Prediction value | Absolute deviation | Reference value | Prediction value | Absolute deviation |
| Meat color (L*, dimensionless) | 46.37 | 45.98 | 0.39 | 44.27 | 45.34 | 1.07 |
| Water holding capacity | 16.60 | 17.14 | 0.54 | 17.33 | 17.96 | 0.63 |
| Moisture content (%) | 76.18 | 76.62 | 0.44 | 76.12 | 75.63 | 0.49 |
| Protein content (%) | 28.45 | 27.82 | 0.63 | 17.31 | 16.82 | 0.49 |
| Fat content (%) | 3.26 | 3.38 | 0.12 | 1.20 | 1.10 | 0.1 |
| Total viable counts (logcfu/g) | 3.95 | 3.78 | 0.17 | 3.68 | 3.85 | 0.17 |
| Total volatile basic nitrogen (mg/100 g) | 9.57 | 9.84 | 0.27 | 12.34 | 13.00 | 0.66 |
| Biogenic amines (cadaverine, mg/100 g) | 28.63 | 28.98 | 0.35 | 31.33 | 28.94 | 0.39 |

It can be seen from the Table 5 and Table 6 that quality index data of the sample by the method of Embodiment 1 is equivalent to that by the method of Comparative example 1.

Although the embodiments of the present disclosure have been disclosed above, the present disclosure is not limited to the applications listed in the specification and the implementations. The present disclosure can be applied to various fields suitable for the present disclosure absolutely, and other modifications can be easily realized by those skilled in the field. Therefore, the present disclosure is not limited to the specific details and the illustrations shown and described herein without departing from the general concepts defined by the claims and equivalent scopes.

What is claimed is:

1. An integrated rapid non-destructive detection system for multi-index of meat quality, comprising:
    a spectrometer, which is configured to obtain near-infrared spectra of a meat sample;
    an industrial tablet computer, comprising:
    an embedding module, which is configured to store prediction models of multiple quality indexes;
    a determining module, which is connected with the embedding module, and is configured to call at least one prediction model;
    a prediction module, which is connected with the spectrometer and the determining module, and is configured to receive the near-infrared spectra of the meat sample and then to predict the quality indexes of the meat sample by applying the prediction models;
    wherein the number of detector elements of the spectrometer is determined according to an ultimate minimal resolution, which is settled and controlled when testing the quality indexes of the meat sample, and it is determined by the following steps:

S1, acquiring spectral data of each sample based on different resolution;

S2, predicting the number of the quality indexes of the system depend on the prediction models stored in the embedding module, for any one of the quality indexes, using the spectral data with a series of resolution and the reference value of the quality index to build a series of prediction models based on chemometrics methods, and calculating a prediction correlation coefficient of corresponding model;

S3, determining an inflection point of the prediction correlation coefficient of any one of the quality indexes at different resolution, and the minimal resolution corresponding to this inflection point being determined as the minimal resolution of the quality index; and S4, determining the maximum of the minimal resolution of all quality indexes as the ultimate minimal resolution;

wherein the industrial tablet computer further comprises:

an adjusting module of reference, in which stored an average spectrum X and a spectral threshold have the same genus with the meat samples, wherein the average spectral X, a local minimum reflectance spectrum (m) and a local maximum reflectance spectrum (M) are calculated based on at least 1000 pieces of near-infrared spectra of the samples belonging to the same genus with the meat samples to be predicted, and the spectral threshold is determined according to the average spectra X, the local minimum reflectance spectrum (m) and the local maximum reflectance spectrum (M);

a black-white adjusting module, which is connected with the adjusting module of reference and the spectrometer configured to obtain N+1 spectra of the samples after N spectra (N is set according to the characteristics of the sample), wherein the Mahalanobis distance is calculated between the average spectra X and the N+1 spectra, the N+1 spectra is determined whether it is normal or not by comparing the Mahalanobis distance and the spectral threshold, and on this account whether to carry out black-and-white adjust is controlled.

2. The integrated rapid non-destructive detection system for multi-index of meat quality according to claim 1, wherein the quality indexes determined include at least three indexes among following indexes which comprises meat color, tenderness, water holding capacity, pH, protein content, fat content, moisture content, total viable counts, total volatile basic nitrogen, UFA, total contents of essential amino acid, and biogenic amines;

wherein a spectral range of 400-1100 nm is used to predict meat color, water holding capacity and the moisture content;

wherein a spectral range of 900-1700 nm is used to predict tenderness, pH, the protein content and the fat content;

wherein a spectral range of 400-1100 nm and 900-1700 nm are combined to predict the total viable counts, the total volatile basic nitrogen, UFA, the total contents of essential amino acid, and the biogenic amines;

acquiring spectral data including 400-1100 nm and 900-1700 nm, wherein the quality indexes are divided into group A predicted by 400-1100 nm and group B predicted by 900-1700 nm, the ultimate minimal resolutions are determined with above methods, respectively.

3. The integrated rapid non-destructive detection system for multi-index of meat quality according to claim 1, wherein a range of different resolution belong to the group A is 0.4-8 nm, and a range of different resolution belong to the group B is 15-45 nm.

4. The integrated rapid non-destructive detection system for multi-index of meat quality according to claim 1, wherein the prediction models of each quality index are built with following steps:

determining a sample set, and measuring the reference value of each prediction index of each sample, wherein the genus of a sample in the sample set is the same as the genus of the meat samples;

determining an acquisition range according to the quality indexes of the meat samples, acquiring all near-infrared spectra of each sample in the sample set, wherein the spectra data in the range of 400-1700 nm are obtained and merged by acquired near-infrared spectra of 400-1100 nm and 900-1700 nm to predict the total viable counts, the total volatile basic nitrogen, UFA, the total contents of essential amino acid, or biogenic amines;

calculating the differences of the near-infrared spectra between adjacent peaks and troughs, sorting to be extracted characteristic spectra, and constructing the spectrogram with sort number as horizontal axis and the foresaid differences as vertical axis;

for any one of the quality indexes to be predicted, building the prediction model by using the characteristic spectra and the reference value of the quality index based on chemometric methods;

wherein the industrial tablet computer also comprises a spectral processing module, which is connected to the spectrometer and configured to extract the feature of spectra from acquired near-infrared spectra, and then the index-prediction module receiving the extracted feature of spectra of the meat sample, and combining with the prediction model to predict the quality index of the meat sample.

5. The integrated rapid non-destructive detection system for multi-index of meat quality according to claim 4, wherein the samples in a calibration set and a prediction set belong to the same genus, the samples in the calibration set are collected from three breeds at least, the samples of each breed include at least 5 kinds of month ages, samples of each month age include at least 5 parts, and samples of each part at least include time points of 45 min, 24 h, 72 h or 120 h after being slaughtered.

6. The integrated rapid non-destructive detection system for multi-index of meat quality according to claim 1, wherein the detection system further comprises:

a dark box, whose top is provided with a detection window, wherein the spectrometer is arranged in the dark box, and a condensing lens and a light source are successively arranged below the detection window from top to bottom;

a black-white adjusting component, which comprises a disc rotationally arranged in the dark box and below the detection window, and a motor configured to drive the rotation of the disc; wherein the disc is provided with a white board, a black board and a through hole, and the motor is connected to the black-white adjusting module to control rotating the disc so that the white board, black board and the through hole are selectively coaxial with the detection window.

7. The integrated rapid non-destructive detection system for multi-index of meat quality according to claim 6, wherein the light source includes two halogen metal reflectors symmetrically arranged at 15-25 mm below the detection window, and the angle between the central axis of each reflector and the detection window is 55°-65°.

8. The integrated rapid non-destructive detection system for multi-index of meat quality according to claim 1, wherein the detection system further comprises: a result display module, which is connected with the prediction module and configured to receive and display prediction results.

9. The integrated rapid non-destructive detection system for multi-index of meat quality according to claim 1, wherein the detection system further comprises: a data transmission module, which is connected with the prediction module and configured to receive and transmit predicted index data to a client.

* * * * *